United States Patent [19]

Paulson

[11] Patent Number: 4,827,217
[45] Date of Patent: May 2, 1989

[54] LOW NOISE CRYOGENIC APPARATUS FOR MAKING MAGNETIC MEASUREMENTS

[75] Inventor: Douglas N. Paulson, Del Mar, Calif.

[73] Assignee: Biomagnetic Technologies, Inc., San Diego, Calif.

[21] Appl. No.: 37,030

[22] Filed: Apr. 10, 1987

[51] Int. Cl.$^4$ ............... G01R 33/035; G01R 33/16; A61B 5/05; G01N 27/72

[52] U.S. Cl. .................... 324/248; 128/653; 324/201; 324/225; 335/216

[58] Field of Search ............... 324/225, 248, 346, 201, 324/204, 224, 340; 128/653; 335/216; 336/DIG. 1

[56] References Cited

U.S. PATENT DOCUMENTS

| | | | |
|---|---|---|---|
| 3,369,174 | 2/1968 | Groenendyke et al. | 324/340 X |
| 3,980,076 | 9/1976 | Wikswo et al. | |
| 4,071,815 | 1/1978 | Zemanek | 324/340 X |
| 4,437,064 | 3/1984 | Overton, Jr. et al. | 324/248 X |
| 4,523,147 | 6/1985 | D'Angelo et al. | 324/248 |
| 4,646,025 | 2/1987 | Martin et al. | 324/248 X |
| 4,689,559 | 8/1987 | Hastings et al. | 324/248 |

OTHER PUBLICATIONS

Brochure of Biomagnetic Technologies Inc., "Introduction to Biomagnetic Measurements and Instruments", 7 pages, published prior to 4/10/86.

D. E. Farrell et al., "Magnetic Measurement of Human Iron Stores," IEEE Trans. on Magnetics, vol. MAG-16, Sep. 1980, pp. 818-823.

Brittenham et al., "Diagnostic Assessement . . . ", Il Nuovo Cimento, vol. 2, 1983, pp. 567-581.

D. E. Farrel et al., "A Clinical System for Accurate Assessment of Tissue Iron Concentration", Il Nuovo Cimento, vol. 2, 1983, pp. 583-593.

Wolfgang Ludwig et al., "Eisenuberladung der Leber--eine Heraus-forderung fur die SQUID-Messtechnik," Postprint of Dornier GmbH (with English translation), dated Jan. 1986, pp. 22 and 23.

Primary Examiner—Gerard R. Strecker
Attorney, Agent, or Firm—Gregory O. Garmong

[57] ABSTRACT

Apparatus for performing sensitive magnetic measurements using cryogenically cooled instrumentation, wherein the instrumentation is separated from the bubbles present in a cryogenic cooling fluid. In one embodiment, the magnetic measurement instrumentation is placed in a tail piece joined by heat conducting bolts to a dewar containing a cryogenic fluid, and heat from the instrumentation is conducted to the cryogenic fluid heat sink by metallic strips reaching to the bolts. The cryogenic fluid does not contact the instrumentation directly, resulting in a significantly reduced level of noise in the instrumentation. The tail piece may also be evacuated to avoid pressure and temperature variations that may cause noise and affect the magnetic instrumentation.

12 Claims, 2 Drawing Sheets

LOW NOISE CRYOGENIC APPARATUS FOR MAKING MAGNETIC MEASUREMENTS

BACKGROUND OF THE INVENTION

This invention relates to cryogenic apparatus, and, more particularly, to cryogenic apparatus for making sensitive magnetic measurements.

The human body produces various kinds of energy that may be used to monitor the status and health of the body. Perhaps the best known of these types of energy is heat. Most healthy persons have a body temperature of about 98.6° F. A measured body temperature that is significantly higher usually indicates the presence of an infection or other deviation from normal good health. A simple medical instrument, the clinical thermometer, has long been available to measure body temperature.

Over 100 years ago, medical researches learned that the body also produces electrical signals. Doctors today can recognize certain patterns of electrical signals that are indicative of good health, and other patterns that indicate disease or abnormality. The best known types of electrical signals are those from the heart and from the brain, and instruments have been developed that measure such signals. The electrocardiograph measures electrical signals associated with the operation of the heart, and the electroencephalograph measures the electrical signals associated with the brain. Such instruments have now become relatively common, and most hospitals have facilities wherein the electrical signals from the bodies of patients can be measured to determine certain types of possible disease or abnormality.

More recently, medical researchers have discovered that the body produces magnetic fields naturally or when properly stimulated, of a type completely different from the other types of energy emitted from the body. The research on correlating magnetic fields and responses with various states of health, disease and abnormality is underway. It has been demonstrated, among other things, that deficiencies or excesses of iron in the body can be determined quantitatively by the paramagnetic response of iron-containing molecules in the liver.

The normal, healthy human body typically contains about 60 milligrams of iron per kilogram of body weight (or about four grams of iron in a typical adult male). A large deficiency or excess of iron in the body can be clinically significant. A deficiency of iron deplete bodily reserves, interfere with hemoglobin production, and lead to anemia in severe cases. An excess of iron can indicate shifts in body chemistry or disease, such as hereditary hemochromatosis, in the early stages of refractory anemias and sometimes in liver disease.

Early diagnosis of iron deficiency or excess imbalances in the body is particularly important, as these problems can often be effectively treated at an early stage. Several techniques have been developed for determining the iron content of the body. Indirect methods involve measurements of the levels of chemicals whose presence and amount are thought to be related to iron level in the body. These methods, such as measurement of serum ferritin or urinary iron excretion, are not sufficiently quantitative to be useful in detecting the early stages of an imbalance. Direct invasive techniques, such as tissue biopsy of the liver, are more quantitative and accurate, but the discomfort and risks associated with their use limit their applicability in screening patients for early indications of iron imbalance.

It has now become possible to make measurements of the iron content of organs, and particularly the liver where iron reserves are stored, by direct magnetic measurements that are noninvasive and therefore particularly suitable for early diagnosis. A biomagnetic susceptometer is an instrument having a magnetic excitation coil which excites a paramagnetic response in iron-containing molecules in the body, and having a very sensitive magnetic detector to measure the paramagnetic response. The biomagnetic susceptometer is placed near to the body of the patient, and the patient's iron levels are measured without any known ill effects on the patient. The patient is unaware of any sensation of measurement, except that he is moved cyclically toward and away from the measurement instrument.

Biomagnetic susceptibility measurements require extraordinarily sensitive and sophisticated magnetic detectors and techniques for avoiding spurious noise signals. The fields to be measured from the liver are typically less than 1/100,000 as great as the magnetic field of the earth in which the instrument and patient are immersed. Nearby electrical equipment, metals, implants, and even the signals from other organs of the body can interfere with the signal obtained from the organ under study.

At the heart of the biomagnetic susceptometer are specialized magnetic field sensing coils, and detectors called Superconducting QUantum Interference Devices (or "SQUIDs"). These devices, which measure very small magnetic signals, operate in the superconducting temperature range for their materials of construction. In the current approach common to most types of superconducting apparatus, the superconducting temperature is achieved with a bath of a cryogenic fluid which is maintained as a liquid but boils to remove heat during operation. The SQUIDS are placed into the cryogenic fluid bath for stabilized operation at the required temperature.

In an existing biomagnetic susceptibility measurement instrument, the magnetic field sensing coils, magnetic excitation coils, and SQUIDs are immersed in a container of liquid helium at a temperature of 4.2° K (i.e., near to absolute zero). The field sensing coils and magnetic excitation coil are placed near the bottom of the container, within a few centimeters of the patient. The container, insulation, and related components are made of special materials that do not interfere with the magnetic measurements. For example, the container itself is made of a fiberglass that has substantially no magnetic susceptibility. The magnetic excitation coil is operated to excite a paramagnetic response in the iron-containing molecules in the patient's liver, and the response is detected by the magnetic field sensing coil and the SQUID working together. The instrumentation is designed to minimize interference from magnetic signals, both steady and varying, other than those for which a measurement is sought.

The existing biomagnetic susceptibility instruments have been shown to give measurements of iron concentration in the liver that correlate very well with measurements made by biopsy or other invasive technique, particularly for conditions of excess iron. However, there is some lack of resolution of the iron content, particularly for iron levels below normal. In these cases, the paramagnetic signal may be masked by spurious fields and influences, and measurement becomes difficult. Complex, expensive electronics can be used to resolve the small signal for the background, with reasonable effectiveness. Magnetically quiet enclosures are also used to reduce the background noise and thence improve resolution of the paramagnetic response of the liver. Nevertheless, there continue to be limits to the resolution possible with existing biomagnetic susceptometers, and it would be desirable to improve the ability of the instruments to detect weak signals.

Thus, there exists a need for an improved apparatus for measuring small biomagnetic responses induced by an external magnetic signal. Such improved technology would also be of value in other areas where weak magnetic responses are studied, such as geology and marine studies. The present invention fulfills this nedd, and further provides related advantages.

SUMMARY OF THE INVENTION

The present invention provides an improved cryogenic apparatus for making measurements of weak magnetic responses and signals, with greatly reduced noise. With this apparatus, the magnetic noise is reduced by a factor of over 100 times as compared with existing approaches, so that magnetic measurements of the human body can be made with great accuracy and resolution. In particular, measurements of iron deficiencies of the liver can be made by non-invasive biomagnetometry techniques.

In accordance with the invention, cryogenic magnetic measurement apparatus comprises an insulated vessel suitable for containing a cryogenic fluid to act as a heat sink; an insulated tail piece having no cryogenic fluid therein, the tail piece being constructed of materials which do not interfere with the taking of magnetic measurements; a thermal connector between the interior the tail piece and the interior of said insulated vessel, the thermal connector being heat conducting to conduct heat from the interior of the tail piece to the interior of the insulated vessel and providing a liquid-tight seal to prevent cryogenic liquid from leaking from the insulated vessel into the tail piece; magnetic measurement apparatus positioned within the tail piece; and means for conducting heat from the magnetic measurement apparatus to the thermal connector, so that in operation heat can be removed from the magnetic measurement apparatus into the thermal connector and thence into the cryogenic liquid heat sink contained with the apparatus.

It has not previously been appreciated and understood, but has now been discovered, that a primary source of the remaining noise in conventional devices for measuring small magnetic signals in large ambient fields is a physical source, bubbles in the cryogenic fluid surrounding the field sensing coils and the SQUIDs. The field sensing coils and SQUIDSs are usually immersed in the cryogenic fluid, which directly contacts and cools these components of the magnetic measurement apparatus. The SQUID operates effectively only in the low, constant temperature possible by this approach. As heat is transferred into the cryogenic liquid, the fluid boils to maintain constant temperature and bubbles are formed. These bubbles rise in the liquid, and the formation and motion of the bubbles, and the environmental susceptibility variations caused thereby, are thought to induce spurious magnetic signals which become noise.

The present invention provides a new design of cooler for the magnetic measurement apparatus. The magnetic measurement apparatus is not immersed in the cryogenic liquid in this apparatus, and the cryogenic liquid therefore does not cool the magnetic measurement apparatus directly. Instead, the magnetic measurement apparatus is operated within an insulated structure called a tail piece that is separate from, but attached to, the insulated vessel for holding the cryogenic liquid, commonly called a dewar. Cryogenic liquid is not introduced into the tail piece. Means for conducting heat, preferably a strip of a metallic conductor such as copper, conducts heat from the magnetic measurement apparatus to a thermal connector between the tail piece and the insulated vessel holding the cryogenic liquid. The heat is thereby transferred to the cryogenic fluid, which boils as it absorbs heat. The cryogenic liquid therefore acts as a heat sink, rather than direct coolant as in prior devices.

In the present approach, there is no cryogenic liquid adjacent to, and bubbling around, the magnetic measurement apparatus in the tail piece, eliminating this source of magnetic noise. The cryogenic liquid in the dewar does bubble, but this activity and magnetic noise are separated sufficiently far from the magnetic measurement apparatus that there is substantially no interference or noise resulting from this effect. Although the initial cooling of the magnetic measurement apparatus by this approach is not as rapid as with the direct cooling approach, it is still sufficient for the purposes of the magnetic measurements.

In a preferred embodiment, cryogenic magnetic measurement apparatus comprises a vertical insulated dewar; an insulated, vertical, hollow tail piece having no cryogenic fluid therein, the tail piece being constructed of materials which do not interfere with the taking of magnetic measurements; a plurality of metallic conductors connecting the dewar and the tail piece, and extending from the interior of the tail piece to the interior of the dewar to conduct heat from the tail piece of the dewar; and magnetic measurement apparatus including a superconducting magnet, a magnetic field sensing coil, and a superconducting quantum interference device positioned within the tail piece.

In a more general aspect of the invention, cryogenic magnetic measurement apparatus comprises insulated container means for holding magnetic measurement apparatus that is operable at cryogenic temperatures; magnetic measurement apparatus contained within the container means; and means for maintaining the magnetic measurement apparatus at cryogenic temperature and for avoiding spurious noise produced by bubbles of vaporized cryogenic fluid. In this form, the invention extends to a technique for avoiding interference produced by bubbles of vaporized cryogenic fluid, based upon the recognition that magnetic susceptibility and pressure variations caused by the bubbles create significant magnetic noise. Techniques such as the use of low pressure gas environments, pumped superfluids, solid cast tail pieces, electronic nullification of the bubble noise by operating at higher frequencies, and physical separation of bubbles that may be produced can be used to effect this result.

In the presently preferred embodiment, the SQUIDs and magnetic coils are operated in conjunction with a liquid helium bath to achieve the necessary low operating temperature required for available superconducting materials. However, as used herein the term "cryogenic" extends to other fluids that may be used to maintain reduced, constant operating temperatures. There have been recent developments in identifying materials having increased maximum superconducting temperatures. These developments suggest that in the future there may be magnetic measurement apparatus operating at liquid nitrogen temperature or even higher temperatures. It is intended that the present invention not be limited to its presently preferred form as used in conjunction with liquid helium cryogenic fluid, but instead cover other cryogenic coolant fluids such as liquid nitrogen or other liquids that maintain a low, constant temperature by boiling. The principle of reduced magnetic noise by avoiding the adverse influence of the bubbles in the fluid is equally applicable to such other cryogenic fluids.

It will now be appreciated that the present invention provides an important advance in the art of magnetic measurement, and particularly in regard to biomagnetic measurements. The magnetic noise which interferes with the measurements has been reduced by a factor of 100 as compared with existing instruments, allowing better measurements of faint magnetic signals. The apparatus, while more complex than conventional dewar systems, can be readily constructed, and easily assembled and disassembled. Other features and advantages of the present invention will be apparent from the following more detailed description, taken in conjunction with the accompanying drawings, which illustrate, by way of example the principles of the invention.

DETAILED DESCRIPTION OF THE PREFERRED EMBODIMENT

Figure 1:
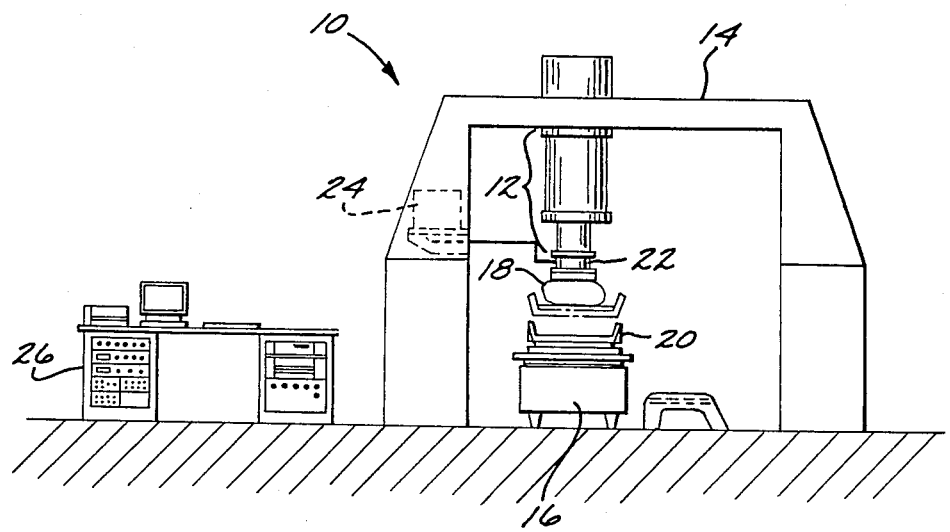
FIG. 1 is an elevational view of the system for making biomagnetic susceptibility measurements.

The preferred embodiment of the present invention is utilized in a biomagnetic susceptometer system 10, illustrated in FIG. 1. An apparatus 12 for performing magnetic measurements, to be described in more detail, is supported in a gantry 14, which is sufficiently wide and tall to permit a patient bed 16 to be rolled under the apparatus 12. The patient, schematically illustrated at numeral 18, lies on a vertically movable platform 20 of the bed 16. A water-filled bag 22, having a water reservoir 24 which provides a supply of water to the bag 22 to keep it properly full, is positioned between the body of the patient 18 and the apparatus 12. A system console 26 is a separate unit having data gathering and control capabilities. In this system 10, the object of the measurements, i.e., the body of the patient, is located completely external to the apparatus 12, as is the case for biomagnetic measurements. However, the object being magnetically measured could be located within the apparatus 12, as where the magnetic characteristics of a small inert object were being studied.

To operate the system 10, a patient 18 is placed onto the bed 16 and moved into place below the apparatus 12, with that portion of the body of the patient to be studied, typically the liver, positioned directly below the apparatus 12. The water bag 22 is positioned between the end of the apparatus 12 and the body of the patient 18, and filled with water to form a continuous water path between the apparatus 12 and the patient 18. Biomagnetic susceptibility measurements are then taken using the apparatus 12. To null out the effect of the background magnetic environment, the platform 20 is slowly raised and lowered as the measurements are taken, as schematically illustrated in FIG. 1. The patient's body, and the particular organ under study, is thereby moved toward and away from the apparatus 12. In subsequent analysis of the data gathered, the organ under study can be viewed as a mass within an environment of the remainder of the patient's body, and the magnetic susceptibility of the remainder of the patient's body must be considered. Water has a magnetic susceptibility similar to that of the remainder of the body of the patient (excluding the organ under study), and the placement of the water bag 22 between the apparatus 12 and the patient 18 reduces the apparent effect of the remainder of the body moving toward and away from the apparatus. That is, use of the water bag creates an apparent measurement environment wherein the organ under study moves in a uniform and constant water/remainder of the body environment. The contribution of the organ itself, and excluding the external environment and the remainder of the patient's body, to the magnetic susceptibility may therefore be understood directly.

This approach to gathering data on the body is noninvasive—no breaking of the skin or intrusion by an instrument is required. The patient need only lie on the bed for the time required to make the measurements. The susceptibility measurements apply to the body a small magnetic field about the intensity of a toy bar magnet, which is not thought to be injurious to the patient in any respect. The gathering of biomagnetic susceptibility data may be made in less than one minute, although a large amount of data is ordinarily taken over a period of about 10-15 minutes to minimize the effect of transient signals and to obtain a sufficiently large data base for analysis of the small magnetic signals.

Figure 2:
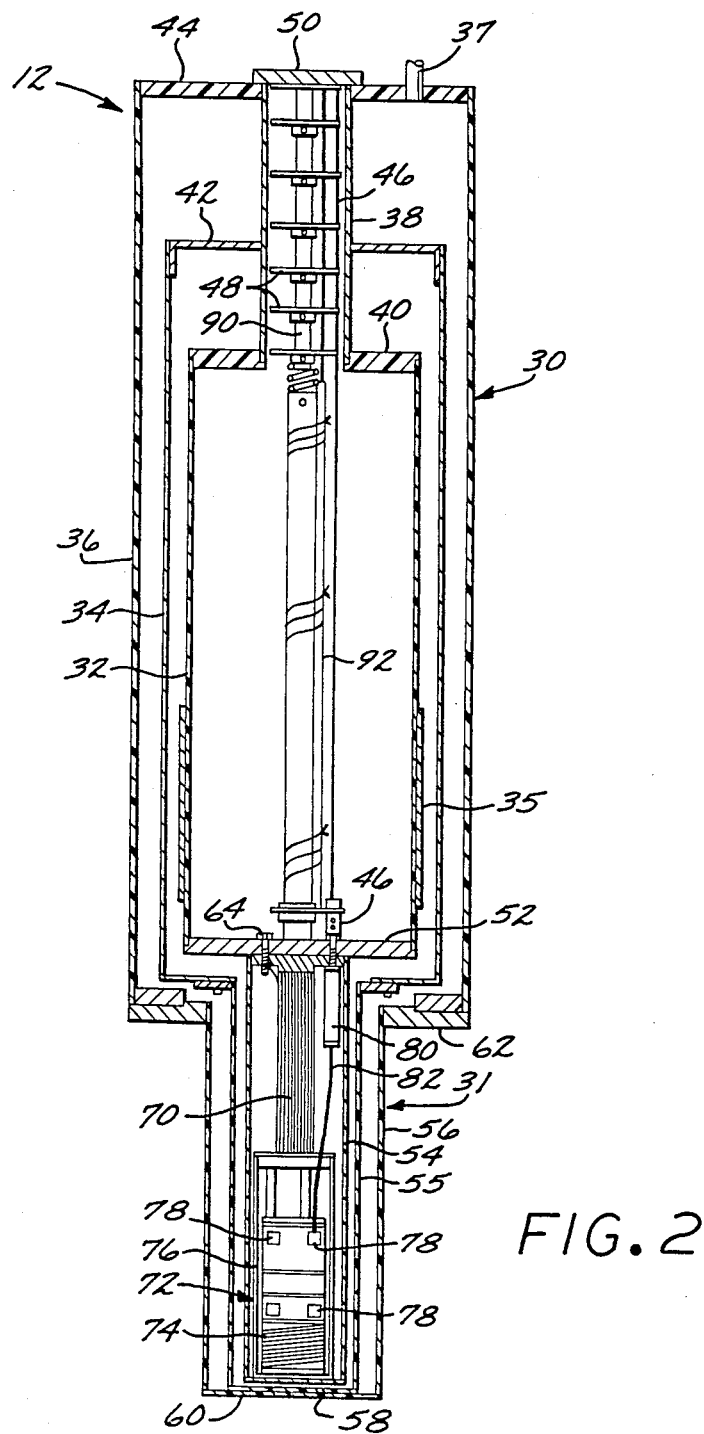
FIG. 2 is a side sectional view of the apparatus for performing magnetic measurements.

The preferred apparatus 12 of the invention, illustrated in section in FIG. 2, comprises two major subassemblies, an insulated vessel 30 and a tail piece 31. These two subassemblies 30 and 31 are joined together in operation, but may be disassembled.

The insulated vessel 30 is similar in construction to a conventional dewar vessel, but is modified in the manner indicated. The vessel 30 includes a cylindrical inner wall 32, a cylindrical middle wall 34, and a cylindrical outer wall 36. The inner wall 32 and the outer wall 36 are constructed of vacuum-tight fiberglass. The middle wall 34 is constructed of vertically aligned thermal conductors, preferably aluminum or copper wires, which serve as a heat conductor to conduct heat upwardly away from the tail piece 31.

The space between the inner wall 32 and the outer wall 36 is insulated with superinsulation 35, preferably aluminized mylar film. (In FIG. 2, the superinsulation 35 is illustrated only in one area for purposes of clarity. However, the superinsulation is found throughout the space between the walls 32 and 34.) The space between the inner wall 32 and the outer wall 36 is vacuum tight, so that a vacuum may be drawn on this space through a port 37. A neck 38 communicating with the interior of the vessel 30 extends upwardly to the top of the vessel 30. Appropriately sized annular closures 40, 42, and 44 close the top ends of the inner wall 32, the middle wall 34, and the outer wall 36, respectively, to the neck 38. The lower end of the vessel 30 is closed in a manner to be described subsequently.

In operation, a cryogenic liquid, preferably liquid helium for presently available superconductor materials, is added to the interior of the vessel 30 through the neck 38. Instrumentation leads 46 are also inserted down the neck 38. A series of heat reflectors 48 in the neck 38 reduce heat loss from the interior of the vessel 30 to the environment through the neck 38, and the top of the neck is closed with an sealed closure 50. The middle wall 34, the superinsulation 35, the outer wall 36, the vacuum between the middle wall 34 and the outer wall 36, the closures 40, 42, and 44, the heat reflectors 48, and the neck closure 50 all aid in minimizing heat loss from the cryogenic liquid within the vessel 30. A support rod 90 extends vertically down the neck 38 to support the instrumentation leads 46, heat reflectors 48, and, optionally, a liquid level detector 92.

The inner wall 32 is closed at the bottom by a circular base plate 52. The base plate 52 is solid, and is sealed to the inner wall 32 by a seal that is not penetrated by the cryogenic liquid. Thus, the interior wall 32 and the base plate 50 in combination form a liquid-tight enclosure for retaining the cryogenic liquid. The base plate 52 is made of a good heat insulator, preferably fiberglass.

The tail piece 31 is a hollow cylinder having a construction similar to that of the vessel 30, including an inner wall 54, a middle wall 55, and an outer wall 56. The outer wall 56 is constructed of a good insulator material that is vacuum tight and does not interfere with the magnetic measurements, preferably a nonmagnetic fiberglass material. The inner wall 54 is constructed of a vertically extending array of metallic conductor wires, preferably 0.005 inch diameter copper wires that act as a radiofrequency interference shield and conduct heat upwardly to the bottom of the vessel 30.

The space between the middle wall 55 and the outer wall 56 is continuous with the space between the inner wall 32 and the outer wall 36 of the vessel 30, and is evacuated through the port 37. The bottom end of the middle wall 55 is closed with a circular closure 58, and the bottom end of the outer wall 56 is closed with a vacuum tight seal to a circular closure 60. Both circular closures 58 and 60 are constructed of a material that does not interfere with the taking of magnetic measurements, preferably nonmagnetic fiberglass.

The top end of the middle wall 55 is flanged outwardly and the bottom end of the middle wall 34 of the vessel 30 is flanged inwardly to provide a structural connection between the two pieces. The top end of the outer wall 56 and the bottom end of the outer wall 36 are connected by a vacuum tight annular closure 62, to form a continuous vacuum tight volume that may be evacuated by pumping on the vacuum port 37.

Heat is removed from the interior of the tail piece 31 to the cryogenic fluid heat sink within the vessel 30 through a plurality of metallic bolts 64, which are preferably constructed of copper or a copper containing alloy for good thermal conduction. The bolts 64 pass upwardly from the volume within the tail piece 31, through the base plate 52, and into the interior of the vessel 30. The tops of the bolts 64 extending into the interior of the vessel 30 contact the cryogenic liquid contained within the vessel 30, which acts as a heat sink for the heat conducted from the interior of the tail piece 31, through the bolts 64, and into the vessel 30.

Heat is conducted for the central volume of the tail piece 31 to the bolts 64 through a means for conducting heat. Preferably, such means is a plurality of metal strips 70 or the like, such as copper strips. The strips 70 are bundled and tied to form a compact, easily handled structure. Preferably, the strips 70 are a commercially available product called Litz wire, which is a compact bundle of about 100 copper wires, each 0.002 inches in diameter. Heat is conducted from the central volume of the tail piece 31 to the bolts 64 through the metal strips 70. The heat is then transferred into the vessel 30 by conduction through the bolts 64. The heat flows into the cryogenic liquid within the vessel 30, causing the cryogenic liquid to boil and carry the heat away up the neck 38.

Magnetic measuremnt apparatus 72 is located within the central volume of the tail piece 31. A magnetization solenoid 74 (also sometimes termed a magnetic excitation coil) is wound in a split pair configuration onto a 1 inch diameter quartz cylinder 76. The magnetization solenoid 74 typically is formed of about 800 turns of 0.007 inch diameter superconducting niobium-titanium wire, and is energized to produce a magnetic field of about 50 Gauss at a distance of 2 centimeters below the bottom of the tail piece 31. A magnetic field sensing coil 78 is also located within the central volume, and supported on the quartz cylinder 76. A superconducting quantum interference device 80, or SQUID, detector is also located within the central volume, and connected to the magnetic field sensing coil 78 through a lead 82. Typically, there are provided a plurality of magnetic field sensing coils 78 and SQUIDs 80 within the tail piece 31.

In operation of the apparatus 12, a paramagnetic response is excited in the iron-containing molecules in the organ under study by the magnetization solenoid 74. The response is received by the magnetic field sensing coil 78 and detected by the SQUID 80. The resulting signal is transmitted to the console 26 from the SQUIDs through instrumentation leads.

It is understood that the removal of heat from the central volume 68 of the tail piece 31 is less efficient by this approach than in the conventional approach of filling the entire apparatus with the cryogenic liquid. However, the principal adverse result of the reduced efficiency is a somewhat longer cool down time at the beginning of an operating cycle. The greater cool down time is not a severe problem, inasmuch as the vessel 30 is ordinarily maintained filled with the cryogenic liquid, and cool down occurs only infrequently. The cryogenic liquid is drained and the system brought to ambient temperatures only for repairs or equipment modification. It is not necessary to drain the system and refill for each patient.

With a well insulated tail piece 31, the interior is maintained within about 2° K. of 4.2° K., the temperature of the preferred liquid helium cryogenic fluid, which is sufficient for operation of the apparatus 12. As used herein, the term "cryogenic temperature" refers to a temperature sufficiently low that superconductivity occurs in the superconducting quantum interference device. At the present time, such temperatures must be less than about 10° K. for the devices to operate. A "cryogenic fluid" or "cryogenic liquid" as used herein is therefore a liquid that boils at a cryogenic temperature. As the technology of superconductors advances, new materials are discovered which permit higher operating temperatures, and in the context of the present invention much higher temperatures would also be considered cryogenic temperatures.

The principal advantageous result of the approach of the present invention is that higher resolution and greater precision can be obtained in the measured small magnetic signals, because the noise induced by the boiling cryogenic liquid are removed. In the preferred embodiment, the magnetic measurement instrumentation is placed in a volume that does not contact the cryogenic fluid, although it is cooled by conductors in contact with the cryogenic fluid. The removal of cryogenic liquid from the vicinity of the magnetic measurement apparatus avoids nucleation of bubbles adjacent such apparatus. The bubbles cause low frequency susceptibility variations adjacent the apparatus as they float upwardly, which can result in erroneous signals. This source of error is eliminated in the present apparatus. Placing the apparatus in a vacumm reduces the possible variation in environmental pressure which has a similar result. For example, in prior apparatus the change in barometric pressure above an open dewar would be sufficient to cause dimensionally induced changes in the magnetic signal output large enough to overwhelm the signal arising from the patient. A further result of the present invention is an increased system time constant, typically about 10 seconds, yielding improved DC stability.

Thus, it is seen that the approach of the present invention yields a significant operating improvement over prior designs. The use of an apparatus which avoids spurious noise produced by bubbles of vaporized cryogenic fluid results in significantly less magnetic noise to interfere with the measurements of very weak magnetic signals. While the invention has been described in relation to a biomagnetic susceptometer and biomagnetic measurements, its applicability extends to other types of measurements such as those in materials science, geology, marine studies, and the like.

Although a particular embodiment of the invention has been described in detail for purposes of illustration, various modifications may be made without departing from the spirit and scope of the invention. Accordingly, the invention is not to be limited except as by the appended claims.

What is claimed is:

1. Cryogenic magnetic measurement apparatus, comprising:
    an insulated vessel whose walls are insulated to prevent the leakage of heat into the interior of said vessel, said vessel having an opening therein whereby a cryogenic fluid may be introduced into the interior of said vessel;
    an insulated tail piece joined to said insulated vessel and having walls that are insulated to prevent the leakage of heat into the interior of said tail piece, said tail piece being constructed of materials which do not interfere with the taking of magnetic measurements;
    a thermal connector between the interior of said tail piece and the interior of said insulated vessel, said thermal connector being heat conducting to conduct heat from the interior of said tail piece to the interior of said insulated vessel and providing a liquid-tight seal to prevent cryogenic liquid from leaking from said insulated vessel into said tail piece;
    magnetic measurement apparatus positioned within said tail piece; and
    means for conducting heat from said magnetic measurement apparatus to said thermal connector, so that in operation heat can be removed from said measurement apparatus to said thermal connector and thence to a cryogenic fluid contained within said vessel.

2. The apparatus of claim 1, wherein said thermal connector comprises metallic bolts extending from the interior said tail piece to the interior of said insulated vessel.

3. The apparatus of claim 2, wherein said metallic bolts include copper.

4. The apparatus of claim 1, wherein said means for conducting heat is a plurality of metal strips connected to said thermal connector at one end, and to said apparatus at the other.

5. The apparatus of claim 4, wherein said metal strips include copper.

6. The apparatus of claim 1, wherein said magnetic measurement apparatus includes a magnetic field sensing coil.

7. The apparatus of claim 1, wherein said magnetic measurement apparatus includes a superconducting quantum interference device.

8. The apparatus of claim 1, wherein said magnetic measurement apparatus includes a magnetization solenoid.

9. Cryogenic magnetic measurement apparatus, comprising:
    a vertical insulated dewar insulated from the external environment;
    an insulated, vertical, hollow tail piece insulated from the external environment, said tail piece being constructed of materials which do not interfere with the taking of magnetic measurements and being joined to said dewar but sealed therefrom so that fluid cannot flow from said dewar into said tail piece;
    a plurality of metallic bolts connecting said dewar and said tail piece, and extending from the interior said tail piece to the interior of said dewar to conduct heat from said tail piece to said dewar;
    magnetic measurement apparatus including a superconducting magnet, a magnetic field sensing coil, and a superconducting quantum interference device positioned within said tail piece; and
    a plurality of metal strips connected to said metallic bolts extending into said tail piece at one end, and to said measurement apparatus at the other, so that heat can be removed from said measurement apparatus to said bolts, and thence into said dewar.

10. The apparatus of claim 9, wherein said magnetic measurement apparatus further includes a magnetization solenoid.

11. The apparatus of claim 9, wherein said bolts include copper.

12. The apparatus of claim 9, wherein said metal strips include copper.

* * * * *